United States Patent [19]

Wilk

[11] Patent Number: 5,360,005
[45] Date of Patent: Nov. 1, 1994

[54] MEDICAL DIAGNOSIS DEVICE FOR SENSING CARDIAC ACTIVITY AND BLOOD FLOW

[76] Inventor: Peter J. Wilk, 185 W. End Ave., New York, N.Y. 10023

[21] Appl. No.: 865,991

[22] Filed: Apr. 9, 1992

Related U.S. Application Data

[63] Continuation-in-part of Ser. No. 819,120, Jan. 10, 1992.

[51] Int. Cl.[5] ............... A61B 5/00; A61B 8/06
[52] U.S. Cl. ............... 128/653.1; 128/661.08; 128/670; 128/773
[58] Field of Search ........... 128/653.1, 660.01, 661.08, 128/662.03, 662.04, 661.1, 660.02, 739, 773, 670, 695; 381/150–151, 205, 169, 188

[56] References Cited

U.S. PATENT DOCUMENTS

| | | |
|---|---|---|
| 4,437,161 | 5/1984 | Anderson . |
| 4,515,164 | 5/1985 | Slavin ............... 128/661.08 |
| 4,641,349 | 2/1987 | Flom et al. . |
| 4,667,335 | 5/1987 | Deindoerfer . |
| 4,770,189 | 9/1988 | Shyu ............... 128/773 |
| 4,777,961 | 10/1988 | Saltzman ............... 128/773 |
| 4,792,145 | 12/1988 | Eisenberg et al. ............... 128/773 |
| 4,838,681 | 6/1989 | Pavlidis . |
| 4,839,822 | 6/1989 | Dormond et al. . |
| 4,878,501 | 11/1989 | Shue ............... 128/773 |
| 4,947,245 | 8/1990 | Ogawa et al. . |
| 4,981,139 | 1/1991 | Pfohl ............... 128/773 |
| 4,989,083 | 1/1991 | Eino . |
| 5,022,402 | 6/1991 | Schieberl et al. ............... 128/773 |
| 5,022,405 | 6/1991 | Hök et al. ............... 128/653.1 |
| 5,025,809 | 6/1991 | Johnson et al. ............... 128/773 |
| 5,027,825 | 7/1991 | Phelps, Sr. et al. ............... 128/773 |
| 5,086,776 | 2/1992 | Fowler, Jr. et al. ............ 128/661.08 |
| 5,140,988 | 8/1992 | Stouffer et al. . |

FOREIGN PATENT DOCUMENTS 3011770 10/1980 Germany ............... 128/773

Primary Examiner—K. M. Pfaffle
Attorney, Agent, or Firm—R. Neil Sudol; Henry D. Coleman

[57] ABSTRACT

A medical diagnostic method comprises the steps of automatically sensing an acoustic vibration inside a person, converting the sensed acoustic vibration to an electrical signal, amplifying the electrical signal, and converting the amplified electrical signal to an acoustic pressure wave. The steps of sensing and converting the sensed acoustic vibration to an electrical signal are implemented by operating an acoustoelectric transducer in a hand held device, and the method further comprises the step of holding the hand held device against a skin surface of the person. The method further comprises the steps of wirelessly transmitting the amplified signal to a receiver and printing or displaying the transmitted acoustic information after a processing thereof. The acoustic information or the processed information derived therefrom is advantageously printed in graphic form. Original acoustic information or processed information may be stored for subsequent use in diagnosing a patient. In another embodiment, the device is further provided with an ultrasonic generator, sensor, and processing circuitry for providing an indication of moving fluid, such as blood.

7 Claims, 5 Drawing Sheets

| 86 | 88 | 90 | 92 | 94 | 96 |
|---|---|---|---|---|---|
| TRANSMITTER CODE | PATIENT CODE | PARAMETER IDENTIFIER | PARAMETER VALUE | MEASURE LOCATION | TIME/ DATE |
FIG. 5
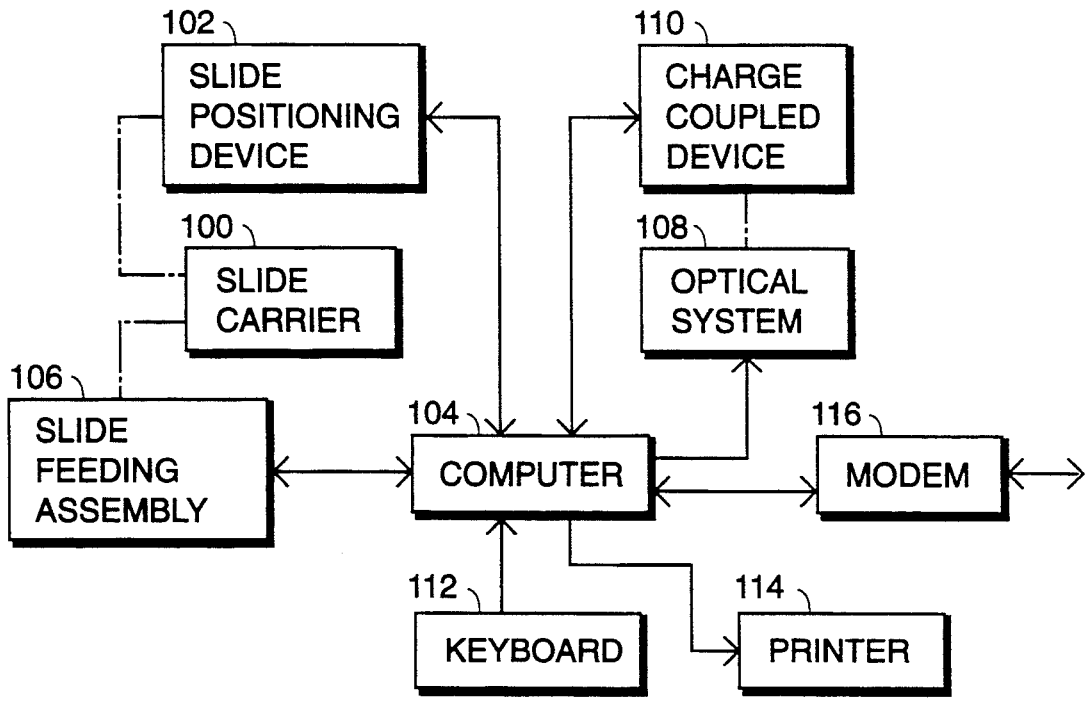
FIG. 6
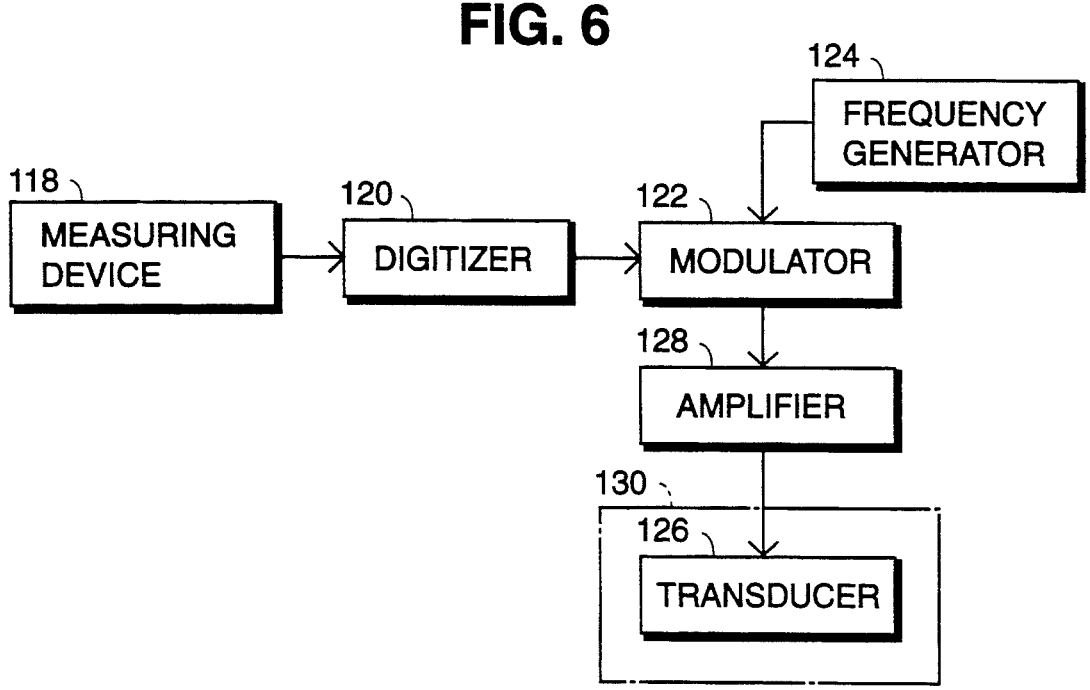
FIG. 7

MEDICAL DIAGNOSIS DEVICE FOR SENSING CARDIAC ACTIVITY AND BLOOD FLOW

CROSS-REFERENCE TO A RELATED APPLICATION

This application is a continuation-in-part of commonly owned application Serial No. 819,120 filed Jan. 10, 1992.

BACKGROUND OF THE INVENTION

This invention relates to a device and an associated method for use in performing medical diagnoses.

A stethoscope is an instrument generally used for monitoring a person's heartbeat to detect irregularities in the functioning of the heart. The stethoscope is also frequently used to monitor the functioning of other organs such as the lungs.

The stethoscope has not changed much in the decades since its introduction into general use. A single user (a physician or nurse practitioner) listens through ear pieces to sounds originating within a patient and calls upon experience and training to interpret the meaning of the sounds.

OBJECTS OF THE INVENTION

An object of the present invention is to provide an improved medical instrument for monitoring acoustic frequency vibrations originating within a person.

Another object of the present invention is to provide such a medical instrument which permits the sensing of internal sounds simultaneously by a plurality of individuals.

Another, more particular, object of the present invention is to provide such a medical instrument which generates a visual display, readout or printout presenting information derived from acoustic frequency vibrations originating inside a person.

A further particular object of the present invention is to provide such a medical instrument which enables at least a partial automatic diagnosis of a patient's condition based upon acoustic or ultrasonic information.

Yet another object of the present invention is to provide a method for monitoring acoustic frequency vibrations originating within a person.

Another object of the present invention is to provide such a method which permits the sensing or monitoring of internal sounds simultaneously by a plurality of individuals.

Another, more particular, object of the present invention is to provide such a method which generates a visual display, readout or printout presenting information derived from acoustic frequency vibrations originating inside a person.

A further particular object of the present invention is to provide such a method which performs an at least partial automatic diagnosis of a patient's condition based upon acoustic or ultrasonic information.

SUMMARY OF THE INVENTION

A medical device comprises, in accordance with the present invention, a casing small enough to hold in one's hand and having a surface adapted for engagement with the skin of a patient, an acoustoelectric transducer mounted to the casing for sensing an acoustic vibration originating within a patient's body and for converting the sensed vibration to a first electrical signal, and a transmitter mounted to the casing and operatively coupled to the transducer for wirelessly transmitting, to a receiver, a second electrical signal incorporating information from the first electrical signal.

The medical device may further comprise an amplifier mounted to the casing and operatively coupled to the acoustoelectric transducer for amplifying the first electrical signal to produce an amplified electrical signal. An electroacoustic transducer is mounted to the casing and is operatively connected at an input to the amplifier for producing an acoustic pressure wave from the amplified electrical signal.

Thus, a plurality of individuals may simultaneously listen to a heart beat, breathing, or other cardiovascular or pulmonary activity. A filter may be mounted to the casing and operatively connected between the amplifier and the electroacoustic transducer for filtering predetermined frequencies from the amplified electrical signal prior to feeding thereof to the electroacoustic transducer.

Pursuant to another feature of the present invention, a processing circuit or analyzer is mounted to the casing and is operatively connected at an input to the acoustoelectric transducer and at an output to the transmitter for reducing, to at least one variable parameter, acoustic information contained in the first electrical signal and for feeding a third electrical signal encoding the parameter to the transmitter for transmission to the receiver.

Pursuant to an additional feature of the present invention, the hand held medical device further comprises an ultrasonic wave generator mounted to the casing for generating an ultrasonic pressure wave, an ultrasonic sensor mounted to the casing for monitoring reflected ultrasonic pressure waves returning to the casing upon generation of the waves by the wave generator, and an ultrasound processing circuit mounted to the casing and operatively connected to the sensor for analyzing reflected ultrasonic pressure waves detected by the sensor. An indicator is mounted to the casing and is operatively connected to the processing circuit for generating a signal sensible by an operator and indicating moving fluid such as blood moving through a blood vessel.

Alternatively, the ultrasonic sensor is operatively connected to the transmitter, whereby a signal encoding ultrasonic information from the sensor may be transmitted to a remote receiver. Such a remote receiver may be located in the same room as the hand held casing and may be disposed inside a housing having a size on the order of a cigarette pack.

A related medical device comprises, in accordance with the present invention, a casing small enough to hold in one's hand and having a surface adapted for engagement with the skin of a patient, an acoustoelectric transducer mounted to the casing for sensing an acoustic vibration originating within a patient's body and for converting the sensed vibration to a first electrical signal, an amplifier mounted to the casing and operatively coupled to the acoustoelectric transducer for amplifying the first electrical signal to produce an amplified electrical signal, and an electroacoustic transducer mounted to the casing and operatively connected at an input to the amplifier for producing an acoustic pressure wave from the amplified electrical signal.

As another feature of this related medical device, a processing circuit is mounted to the casing and is operatively connected at an input to the acoustoelectric transducer for reducing, to at least one variable parameter, acoustic information contained in the first electrical signal and for generating an additional electrical signal encoding the parameter. The processing circuit is operatively connected to an output component mounted to the casing. The output component provides a sensible output of the derived parameter in response to the additional electrical signal. The output component may include a display or a printer which presents the derived parameter on a film material such as paper.

The derived parameter may have a continuously varying magnitude, such as represented in conventional pulse rate signals, electrical cardiograms etc. In that case, the visual display or printout may include a graph.

A medical device in accordance with another feature of the invention comprises a housing, a receiver mounted to the housing for receiving a wireless electrical signal encoding acoustic information originating inside a person, a memory, a processing circuit, and an oputput component. The memory is mounted to the housing and is operatively connected to the receiver for storing in electrically encoded form the acoustic information contained in the signal. The processing circuit is mounted to the casing and is operatively connected at an input to at least one of the receiver and the memory for reducing, to at least one variable parameter, acoustic information contained in the wireless electrical signal and for generating an additional electrical signal encoding the parameter. The output component is mounted to the housing and is operatively connected to the processing circuit for providing a sensible output of the parameter.

This medical device is preferably portable, and more preferably of a size that can be carried within a coat or breast pocket. The device receives a wireless signal from a hand held acoustic monitoring unit, performs at least a rudimentary analysis of the acoustic information contained in the wireless signal, and provides a preferably visual output of the derived or processed information. The output component may take the form of a small printer or a LCD type display. In this manner, a physician or other user can obtain immediate information in visually readable form, to reinforce or replace the acoustic type input from a conventional stethoscope. Thus, in accordance with the present invention, information is at least partially processed or analyzed prior to use by the physician. Moreover, as discussed in detail hereinafter, the portable medical device may contain a memory which stores previously collected information on the same patient. The prior graphs or parameterized data may be displayed or printed together with currently or recently collected data, thereby facilitating diagnosis as to a possibly changing condition. Furthermore, the memory may contain previously collected acoustic information from multiple patients, together with diagnoses of the acoustic symptoms. The portable medical device may thus provide automated diagnoses for the physician.

The portable medical diagnosis device may further comprise an amplifier mounted to the housing and operatively coupled to the receiver for generating an amplified signal containing the acoustic information. In that event, an electroacoustic transducer or speaker is mounted to the housing and is operatively connected at an input to the amplifier for producing an acoustic pressure wave from the amplified signal.

The amplifier may be operatively connected to the memory for amplifying an acoustic frequency signal stored therein. That acoustic frequency signal may have been recorded during a previous examination of the patient, for example, days, weeks or months prior.

According to another feature of the present invention, an input component such as a keyboard is mounted to the housing and is operatively connected to the memory for storing therein information identifying the person in whom the acoustic information originated.

A medical diagnostic method comprises, in accordance with the present invention, the steps of (a) automatically sensing an acoustic vibration inside a person, (b) converting the sensed acoustic vibration to an electrical signal, (c) amplifying the electrical signal, and (d) converting the amplified electrical signal to an acoustic pressure wave.

The steps of sensing and converting the sensed acoustic vibration to an electrical signal are generally implemented by operating an acoustoelectric transducer in a hand held device, and the method further comprises the step of holding the hand held device against a skin surface of the person.

The amplification of the electrical signal encoding acoustic information may be implemented by operating an amplifier in the hand held device, while conversion of the amplified electrical signal to an acoustic pressure wave is performed by operating an electroacoustic transducer mounted to the hand held device.

Alternatively, prior to or subsequently to the amplification of the electrical signal, it may be wirelessly transmitted to a receiver. The conversion to a pressure wave is then performed by operating an electroacoustic transducer connected to the receiver.

Pursuant to another feature of the present invention, the method further comprises the steps of wirelessly transmitting the amplified signal to a receiver and printing the acoustic information after the step of transmitting. The acoustic information or information derived therefrom during a processing step is advantageously printed in graphic form. In such a processing step, acoustic information contained in the electrical signal or amplified signal is analyzed to derive a value of at least one parameter related to the health of the person. The parameter is then displayed or printed in digital or graphic form.

Pursuant to another feature of the present invention, the medical method includes the step of storing acoustic information contained in the electrical signal.

An acoustic vibration which is the subject of the method may be cardiovascular in nature, for example, if the hand held device is placed against a person's skin near the heart or an artery, for example, in the perons's neck. Alternatively, the acoustic vibration may be pulmonary in nature.

Where the acoustic information pertains to the heart, a parameter obtained during automatic processing may be related to the rate and/or strength of the heart beat. A graphic display or printout of the heart beat contains peaks and valleys as in conventional cardiograms. Similar graphs may be produced as to pulmonary functioning or blood flow through an artery.

A medical instrument in accordance with the present invention for monitoring acoustic frequency vibrations originating within a person permits the sensing of internal sounds simultaneously by a plurality of individuals. Moreover, acoustic information is supplemented by a visual presentation. The visual information may be derived by automatically processing the electrical signal containing the acoustic information. Because information as to previous diagnoses may be stored and compared with current acoustic input, the visual readings can provide diagnostic information, aiding the physician or other practitioner.

BRIEF DESCRIPTION OF THE DRAWINGS

FIG. 5 is a diagram showing the composition of a data string or module used in the system of FIG. 4.

FIG. 6 is a block diagram of a computerized slide scanning system.

FIG. 7 is a block diagram of a device for measuring a diagnostic parameter and transmitting the measurement over the telephone lines.

DETAILED DESCRIPTION

Figure 1:
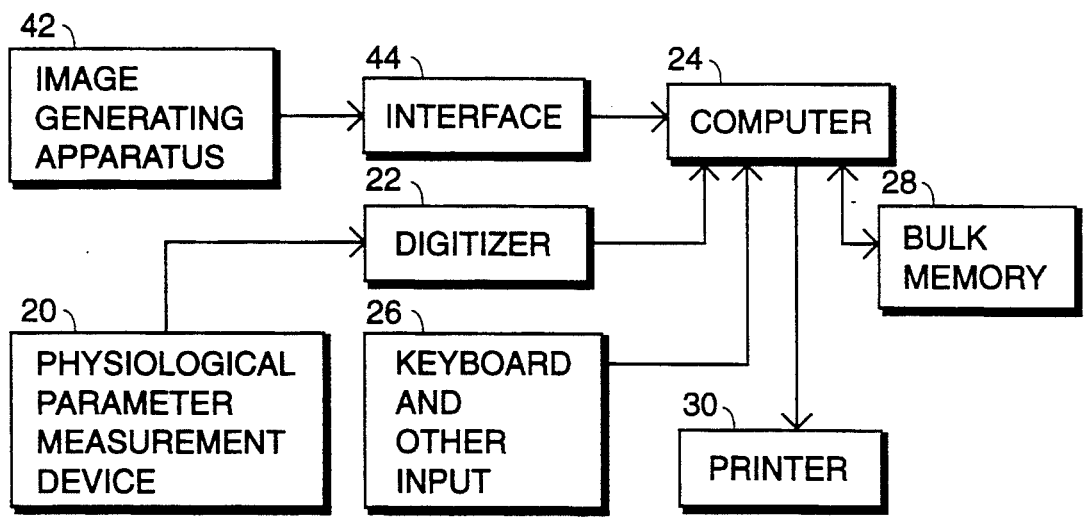
FIG. 1 is a block diagram of a medical diagnostic system.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a doppler study apparatus, an EEG machine, an EKG machine, an EMG machine, a pressure measurement device, an acoustic sensor, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer 22 may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
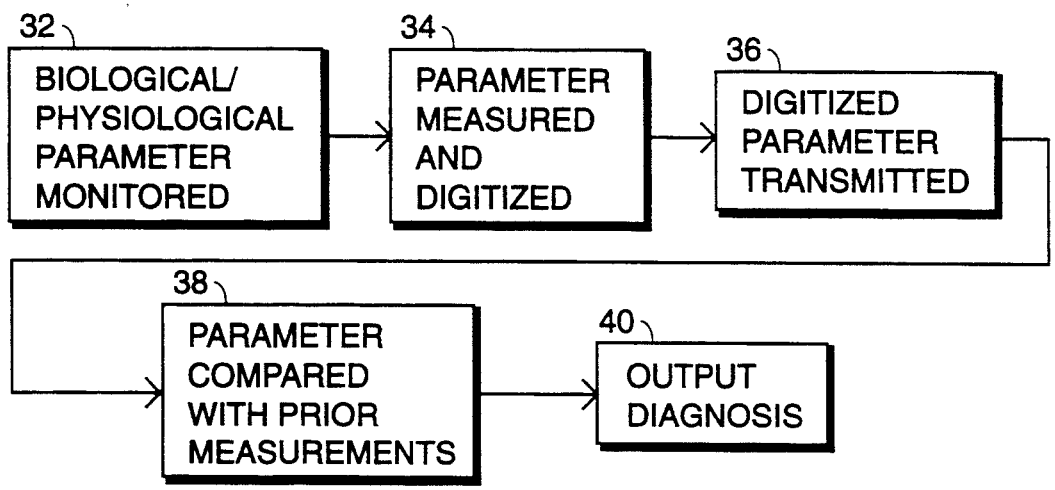
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, an image generating apparatus or scanner 42 for generating in electrically encoded form a visually readable image of an organic part of the patient. Scanner 42 may take the form of an MRI apparatus, a CAT scanner, an X-ray machine, an ultrasonography apparatus, or a video camera with or without magnification optics for magnifying a sample on a slide. The video camera can be used for obtaining an image of a portion of a patient's skin.

Scanner 42 is connected via an interface 44 to computer 24.

Figure 3:
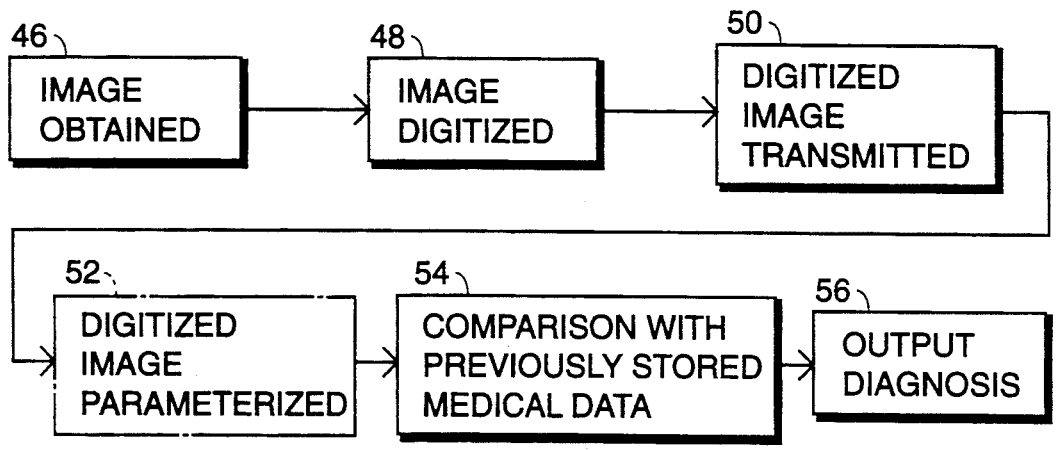
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus or CAT scanner, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 56 (FIG. 3), computer 24 communicates the results of its diagnostic evaluation to a user or patient.

Figure 4:
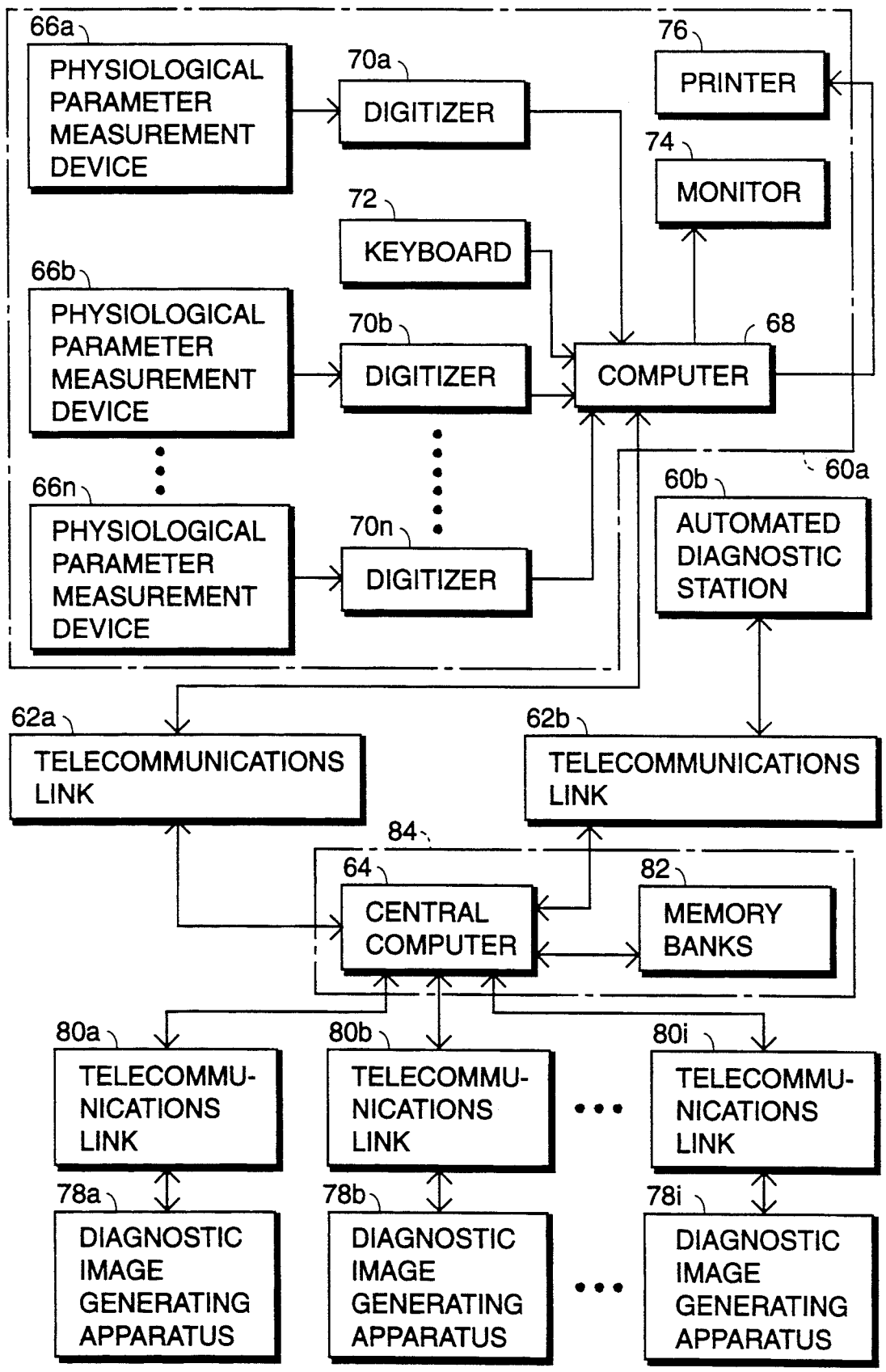
FIG. 4 a block diagram of a further medical diagnostic system.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may resepctively take the form of an electronic thermometer, an electronic blood pressure gauge, a pulmonary function apparatus, a doppler study apparatus, an EEG machine, an EKG machine, an EMG machine, a pressure measurement device, an acoustic sensor, etc.

Digitizers 70a, 70b, . . . 70n convert normally analog type signals into coded binary pulses and transmit the resulting digital measurement signals to computer 68. Digitizers 70a, 70b, . . . 70n may be incorporated into the housings or casing (not shown) enclosing all or part of the respective monitoring and measuring devices 66a, 66b, . . . 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, . . . 78i are also connected to central computer 64 via respective telecommunications links 80a, 80b, . . . 80i. Scanners 78a, 78b, . . . 78i each generate in electrically encoded form a visually readable image of an organic part of the patient. Scanners 78a, 78b, . . . 78i may each take the form of an MRI apparatus, a CAT scanner, an X-ray machine, an ultrasonography apparatus, or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

As illustrated in FIG. 5, local computers 24 and 68 transmit information to central computer 64 in data packets or modules each includes a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures. The texture and line scanning is repeated at different magnification levels.

Computer 104 may be connected to a keyboard 112, a printer 114, and a modem 116. Modem 116 forms part of a telecommunications link for connecting computer 104 to a remote data processing unit such as computer 64 in FIG. 4.

Image generating apparatus 42 in Fig. 1 may take the form of the computerized slide scanning system of FIG. 6.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a doppler study apparatus, an EEG machine, an EKG machine, an EMG machine, a pressure measurement device, an acoustic sensor, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electroacoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in Fig. 4) which utilizes the incoming data to perform a diagnostic evaluation on the patient.

Monitoring and measuring device 118 may include traditional medical instrumentation such as a stethoscope or modern devices such as a CCD.

Figure 8:
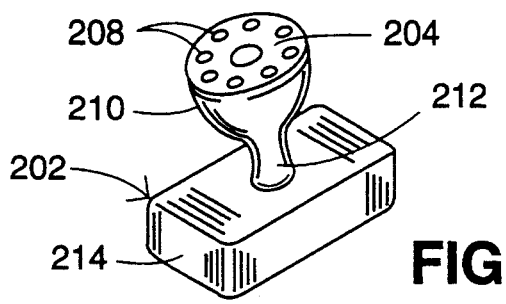
FIG. 8 is a schematic perspective view of a hand held acoustic monitoring device in accordance with the present invention.
Figure 9:
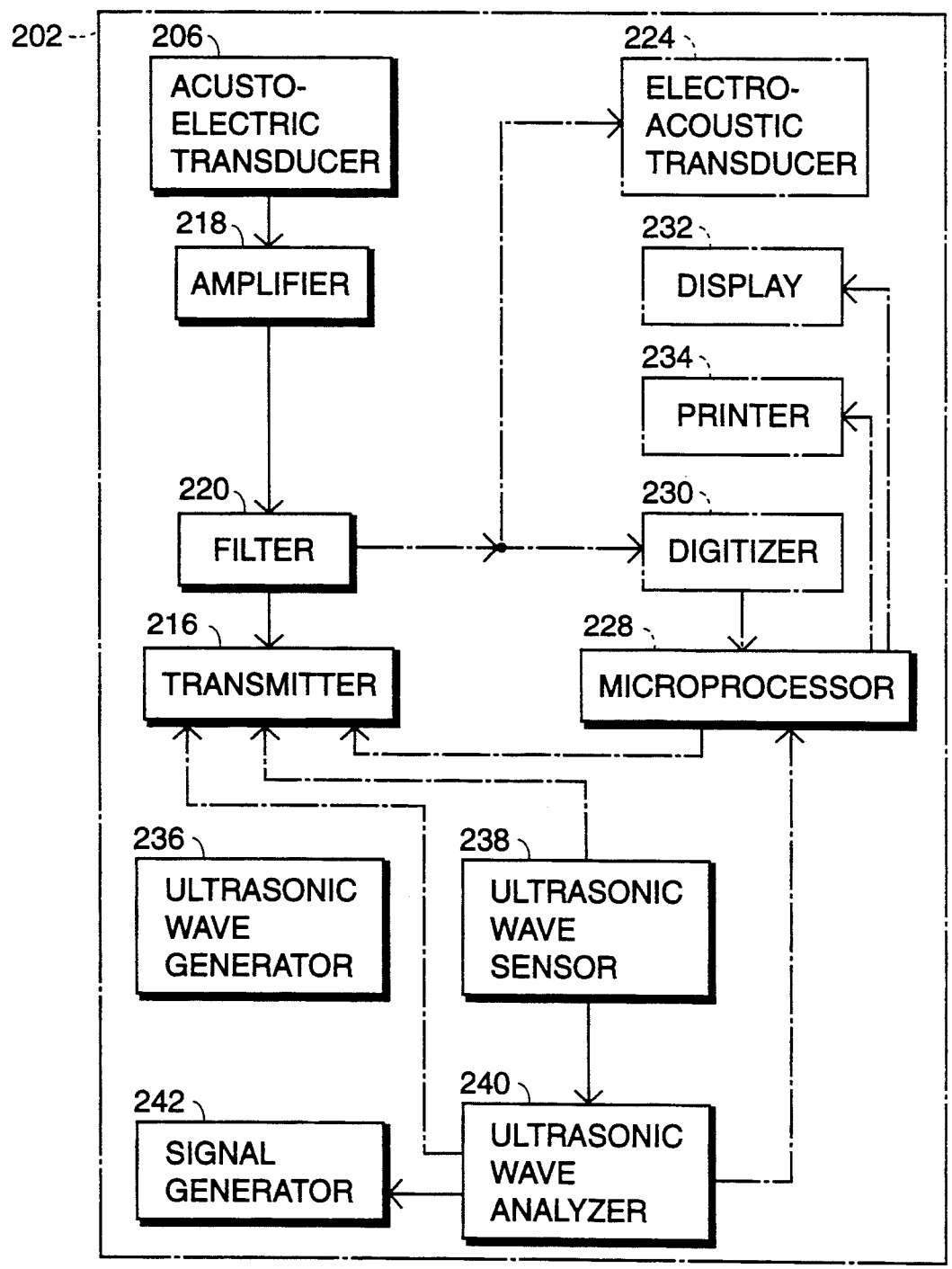
FIG. 9 is a block diagram of functional components of the device of FIG. 8.

As illustrated in FIG. 8, a medical device for monitoring acoustic frequency vibrations originating inside a patient comprises a casing 202 small enough to hold in one's hand and having a surface 204 adapted for engagement with the skin of the patient. As shown in FIG. 9, an acoustoelectric transducer or microphone 206 is mounted to casing 202 in juxtaposition to apertures 208 in surface 204 for sensing an acoustic vibration originating within the patient's body and for converting the sensed vibration to an electrical signal.

Transducer 206 is disposed inside a substantially semispherical portion 210 (FIG. 8) of casing 202 adapted for fitting within a physician's palm. A neck portion 212 of casing 202 connects semishperical portion 210 to a rounded prismatic body portion 214. Prismatic body portion 214 is small enough to be grasped by a human hand, while casing 202 in its entirety is small enough to fit within a coat pocket.

The acoustic monitoring device of FIGS. 8 and 9 further comprises a transmitter 216 mounted to casing 202 and operatively coupled to transducer 206 via an amplifier 218 and a filter 220 for wirelessly transmitting, to a receiver 222 (FIG. 11), an electrical or electromagnetic signal incorporating information from the signal at the output of transducer 206.

Amplifier 218 is mounted to casing 202 and is operatively coupled to transducer 206 for amplifying the electrical signal from transducer 206 to produce an amplified electrical signal. Filter 220 is also mounted to casing 202 and is operatively coupled between amplifier 218 and transmitter 216 for filtering predetermined frequencies from the amplified electrical signal prior to feeding thereof to transmitter 216.

The medical device of FIGS. 8 and 9 may be optionally provided with an electroacoustic transducer or speaker 224 mounted to casing 202 and operatively linked at an input to amplifier 218 via filter 220 for producing an acoustic pressure wave from the amplified electrical signal. That pressure wave essentially reproduces an acoustic frequency packet sensed by transducer 206. Transducer 224 enables a plurality of individuals to simultaneously hear a heart beat, breathing, or other cardiovascular or pulmonary activity upon the juxtaposition of surface 204 to a patient's skin and upon activation of the device (power switch not shown).

Figure 11:
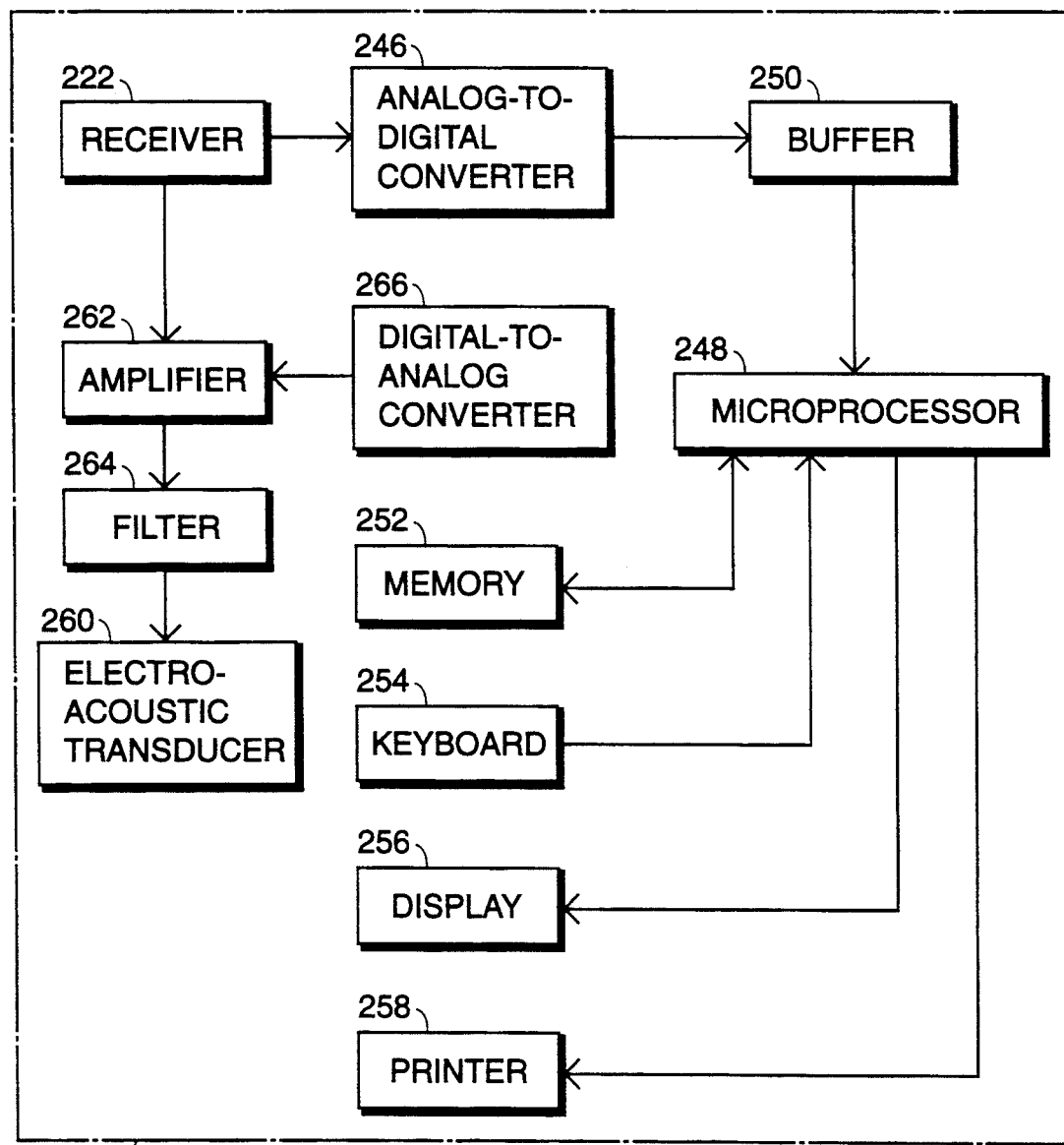
FIG. 11 is a block diagram of functional components of the device of FIG. 10.

Optionally, a microprocessor 228 is mounted to casing 202 and is tied at an input to acoustoelectric transducer 206 via amplifier 218, filter 220, and a digitizer or analog-to-digital converter 230. Microprocessor 228 analyzes acoustic information in an incoming digitized electrical signal and reduces the acoustic information to values of at least one varying parameter. That information may be fed in electrically encoded form to transmitter 216 for wireless transmission to receiver 222 (FIG. 11). Alternatively, the varying computed values of the physiological parameter may be displayed on a small LCD display 232 optionally incorporated into prismatic body portion 214 of casing 202. If prismatic body portion 214 is large enough, it may additionally or alternatively incorporate a printer 234 for providing a graphic or digital printout of the processed acoustic information.

As further illustrated in FIG. 9, the hand held medical device further comprises an ultrasonic wave generator 236 mounted to casing 202 for generating an ultrasonic pressure wave. An ultrasonic sensor 238 is provided in casing 202 for monitoring reflected ultrasonic pressure waves returning to the casing upon generation of the waves by wave generator 236. An ultrasound processing circuit or wave analyzer 240 inside casing 202 is connected to sensor 238 for analyzing reflected ultrasonic pressure waves detected by the sensor. A signal generator 242 such as a dedicated speaker is connected to processing circuit 240 for generating a sound indicative of moving fluid such as blood moving through an artery in a patient's neck.

Alternatively, ultrasonic sensor 238 or processing circuit 240 is linked to transmitter 216, whereby a signal encoding ultrasonic information may be transmitted to remote receiver 222. Receiver 222 is generally located in the same room as the hand held casing 202.

Figure 10:
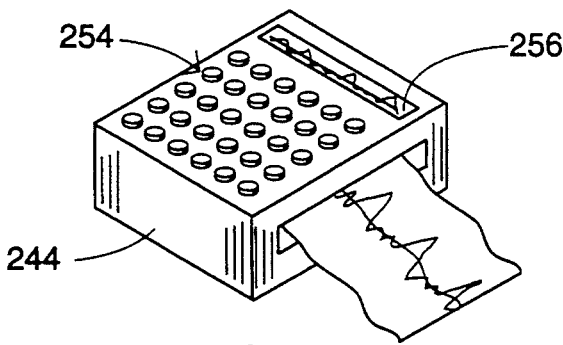
FIG. 10 is schematic perspective view of a portable diagnostic and printout device which cofunctions with the device of FIG. 8 to provide readable results of acoustic measurements and automatic diagnoses, in accordance with the present invention.

A medical device cooperating with the device of FIGS. 8 and 9 to produce, in visually readable form, information derived from acoustic vibrations within a person is illustrated in FIGS. 10 and 11. A pocket size prismatic housing 244 carries receiver 222 which is adapted to receive a wireless electrical signal emitted by transmitter 216 (FIG. 9). Housing 244 also contains a digitizer or analog-to-digital converter 246 which is connected to a microprocessor 248 via a buffer register 250. Incoming electrical signals encoding acoustic information are stored by microprocessor 248 in a memory 252. Memory 252 is sufficiently dense to store electrical signals encoding acoustic information previously collected via the components of FIGS. 9 and 11.

Microprocessor 248 is connected at an input to a keyboard 254 by which identification information such as patient name and birth date may be entered and stored in memory 252. Memory 252 is thereby capable of storing the results of acoustic measurements made at different times, separated, for example, by days, weeks or longer.

Mounted to housing 244 and contained therein are an LCD type display 256 and a printer 258. In response to signals from microprocessor 248, display 256 shows in digital or graphic form the values of heart rate and cardiovascular rhythms, in the event that the device of FIGS. 8 and 9 is used as a stethoscope to monitor cardiovascular activity.

Microprocessor 248 serves to reduce, to at least one variable parameter, acoustic information contained in the wireless electrical signal received by receiver 222 from transmitter 216. For example, microprocessor 248 may be programmed to calculate the amount of energy in the acoustic transmissions from the patient. This energy is an indicator, for example, of cardiac activity where transducer 206 (FIG. 9) is held to a patient's chest over the heart. In the instance where transducer 206 is juxtaposed to a skin surface over an artery, the energy indicator is a measure of blood flow through the artery and can be used to sense obstructions, aneurysms, etc.

Microprocessor 248 generates an electrical signal encoding the continuously computed parameter, whereby successive values of the parameter may be stored in memory 252, displayed on display 256 or printed out via printer 258. In addition, micro-processor 248 may be programmed to compute a more global indicator or parameter such as a heart rate value, or a magnitude indicative of heart beat regularity or rhythm. Such a global parameter may be shown as a digital value on display 256 or on a tabulation produced via printer 258.

Through the use of the wireless stethoscope type device of FIGS. 8 and 9 and the cooperating receiver and output package of FIGS. 10 amd 11, a physician or other user can obtain immediate information in visually readable form, to reinforce or replace acoustic information of the type obtainable from a conventional stethoscope. In addition, that visually decipherable diagnostic information, as well as amplified acoustic information from speaker 224 (FIG. 9) or a speaker 260 in housing 244, is available to more than one individual simultaneously, thereby enabling immediate consultation between a plurality of physicians or other practitioners.

Speaker or electroacoustic transducer 260 receives input from receiver 222 via an amplifier 262 and a filter 264. That input is converted in real time to audible pressure waves. Where speaker 260 is provided, transducer 224 (FIG. 9) may be omitted. Speaker 260 is also operatively connected via amplifier 262, filter 264 and a digital-to-analog converter 266 to memory 252, whereby, under the control of microprocessor 248, speaker 260 is empowered to play back sounds previously recorded in the memory, such as prior cardiovascular sounds of a same patient.

Memory 252 naturally stores successive values of the acoustic parameters calculated via processing operations in microprocessor 248. This parameterized or processed information is also avaliable for subsequent production on display 256 or via printer 258, advantageously in juxtaposition with recently recorded and processed information. Thus, a physician is able to immediately compare a current measurement with a prior measurement of heart, lung or other internal activity of the same patient. Of course, the information is organized in memory 252 by microprocessor 248 in accordance with identification information fed to the microprocessor via keyboard 254.

As discussed in detail hereinabove with reference generally to FIGS. 1-7, memory 252 may store previously collected acoustic information from multiple patients, together with diagnoses of the acoustic symptoms. Thus, microprocessor 248 accessing the records in memory 252 may provide automated diagnoses for consideration by the physician in arriving at his or her diagnoses.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical device comprising:
   a casing small enough to hold in one's hand, said casing having a surface adapted for engagement with the skin of a patient;
   acoustoelectric transducer means mounted to said casing for sensing an acoustic vibration originating within the patient and for converting the sensed vibration to a first electrical signal;
   transmitter means mounted to said casing and operatively coupled to said transducer means for wirelessly transmitting, to a receiver, a second electrical signal incorporating information from said first electrical signal;
   ultrasonic wave generating means mounted to said casing for generating an ultrasonic pressure wave; and
   ultrasonic sensor means mounted to said casing for detecting a reflected ultrasonic pressure wave returning to said casing upon generation of said wave by said wave generating means, said transmitter means being operatively connected to said sensor means for transmitting a signal encoding ultrasonic information from said sensor means.

2. The device defined in claim 1, further comprising amplification means mounted to said casing and operatively coupled to said acoustoelectric transducer means for amplifying said first electrical signal to produce an amplified electrical signal, also comprising electroacoustic transducer means mounted to said casing and operatively connected at an input to said amplification means for producing an acoustic pressure wave from said amplified electrical signal.

3. The device defined in claim 2, further comprising filter means mounted to said casing and operatively connected between said amplification means and said electroacoustic transducer means for filtering predetermined frequencies from said amplified electrical signal prior to feeding thereof to said electroacoustic transducer means.

4. The device defined in claim 1, further comprising analyzing means mounted to said casing and operatively connected at an input to said transducer means and at an output to said transmitter means for reducing, to at least one variable parameter, acoustic information contained in said first electrical signal and for generating a third electrical signal encoding said parameter and feeding said third electrical signal to said transmitter means for transmission to said receiver.

5. The device defined in claim 1, further comprising modulator means operatively connected to said acoustoelectric transducer means and said transmitter means for modulating said second electrical signal with said first electrical signal.

6. The device defined in claim 1 wherein said casing includes a holder portion adapted for a manual grasping and another portion with said surface.

7. A medical device comprising:
a casing small enough to hold in one's hand, said casing having a surface adapted for engagement with the skin of a patient;
acoustoelectric transducer means mounted to said casing for sensing an acoustic vibration originating within the patient and for converting the sensed vibration to a first electrical signal;
transmitter means mounted to said casing and operatively coupled to said transducer means for widely transmitting, to a receiver, a second electrical signal incorporating information from said first electrical signal;
ultrasonic wave generating means mounted to said casing for generating an ultrasonic pressure wave;
ultrasonic sensor means mounted to said casing for detecting a reflected ultrasonic pressure wave returning to said casing upon generation of said wave by said wave generating means;
ultrasound analyzing means mounted to said casing and operatively connected to said sensor means for analyzing the reflected ultrasonic pressure wave detected by said sensor means; and
indicator means mounted to said casing and operatively connected to said analyzing means for generating a signal sensible by an operator and indicating moving fluid.

* * * * *

UNITED STATES PATENT AND TRADEMARK OFFICE
CERTIFICATE OF CORRECTION

PATENT NO.   :   5,360,005
DATED        :   November 1, 1994
INVENTOR(S)  :   Peter J. Wilk It is certified that error appears in the above-indentified patent and that said Letters Patent is hereby corrected as shown below:

Column 6, line 25, replace "28" with --24--.

Column 7, line 15, replace "30" with --28--; line 26, insert --28-- after "memory".

Column 8, line 36, insert --,-- after "modules", replace "includes" with --including--.

Column 11, line 41, replace "amd" with --and--.

Column 14, line 4, claim 7, replace "widely" with --wirelessly--.

Signed and Sealed this

Thirtieth Day of May, 1995

BRUCE LEHMAN

*Attest:*

*Attesting Officer*   *Commissioner of Patents and Trademarks*